United States Patent
Michels et al.

(10) Patent No.: US 6,639,022 B2
(45) Date of Patent: Oct. 28, 2003

(54) PROCESS FOR THE PREPARATION OF SUPERABSORBENT POLYMERS FROM POLYACRYLONITRILES

(75) Inventors: Gisbert Michels, Leverkusen (DE); Thomas Gross, Heiligenhaus (DE)

(73) Assignee: Bayer Aktiengesellschaft, Leverkusen (DE)

( * ) Notice: Subject to any disclaimer, the term of this patent is extended or adjusted under 35 U.S.C. 154(b) by 82 days.

(21) Appl. No.: 09/835,666

(22) Filed: Apr. 16, 2001

(65) Prior Publication Data

US 2001/0044501 A1 Nov. 22, 2001

(30) Foreign Application Priority Data

Apr. 20, 2000 (DE) .......................................... 100 19 756

(51) Int. Cl.$^7$ ............................................... C08F 120/44
(52) U.S. Cl. .................... 525/329.1; 525/194; 525/221; 525/238; 525/329.2; 525/329.3; 525/340; 525/343; 525/344; 525/355; 525/374; 525/383; 525/384; 525/386; 525/212
(58) Field of Search ....................... 524/555; 525/329.1, 525/194, 221, 238, 329.2, 329.3, 340, 343, 344, 355, 374, 386, 383, 384, 212

(56) References Cited

U.S. PATENT DOCUMENTS

| 4,130,525 | A | * | 12/1978 | Kobashi et al. .............. 524/869 |
| 5,356,985 | A | | 10/1994 | Sackmann et al. .......... 524/460 |
| 5,393,845 | A | | 2/1995 | Korte et al. ................. 525/369 |
| 5,728,774 | A | | 3/1998 | Sackmann et al. .......... 525/196 |
| 6,156,848 | A | | 12/2000 | Sackmann et al. ....... 525/329.1 |
| 6,288,158 | B1 | * | 9/2001 | Schapowalov et al. ..... 523/204 |

FOREIGN PATENT DOCUMENTS

DE 198 05 447 8/1999

* cited by examiner

Primary Examiner—Judy M. Reddick
(74) Attorney, Agent, or Firm—Joseph C. Gil; James R. Franks

(57) ABSTRACT

A process for the preparation of superabsorbent polymers by alkaline hydrolysis of polyacrylonitrile emulsions is disclosed. In an embodiment of the invention the process comprise preparing a PAN emulsion, subjecting the emulsion to alkaline hydrolysis, neutralizing the hydrolysate followed by drying, granulation and modifying the surface of the granular polymer by crosslinking. The process is characterized in that the isolation of the superabsorbent polymer entails neither alcohols nor organic solvents.

19 Claims, No Drawings

US 6,639,022 B2

PROCESS FOR THE PREPARATION OF SUPERABSORBENT POLYMERS FROM POLYACRYLONITRILES

FIELD OF THE INVENTION

The invention relates to a process for the preparation of superabsorbent polymers (SAP) by alkaline hydrolysis of polyacrylonitrile emulsions (PAN emulsion).

BACKGROUND OF THE INVENTION

Superabsorbent polymers are known and are used mainly in the manufacture of nappies and incontinence articles, but also as water-storage materials in agriculture and in the covering of electric cables. In general, those superabsorbent polymers are wide-mesh crosslinked, water-insoluble polymers or copolymers based on alkali metal salts of polyacrylic acid or copolymers of alkali metal salts of acrylic acid and acrylamide, which are obtained by the free-radical initiated copolymerization of acrylic acid and polyfunctional monomers, such as divinylbenzene, ethylene glycol dimethacrylate, ethylene glycol diallyl ether, butanediol diacrylate, hexanediol dimethacrylate, polyglycol diacrylate, trimethylolpropane diacrylate, allyl acrylate, diallyl acrylamide, trisallylamine, diallyl ether, methylenebisacrylamide and N-methylol-acrylamide. Owing to their structure, such polymers are capable, by swelling and the formation of hydrogels, of absorbing large quantities of water and aqueous solutions and of retaining them even under pressure.

It is known from DE-A 196 00 163 that SAP's can be prepared by hydrolysis of finely particulate PAN emulsions. It is described that superabsorbent polymers from PAN emulsions can be prepared in a continuous and reproducible manner from concentrated emulsions if self-cleaning reactors having a volume sufficient for a dwell time (residence time) of from 0.5 to 2 hours are used for the alkaline hydrolysis of the PAN emulsion.

It is also described that suitable devices for the preparation of superabsorbent polymers by hydrolysis of PAN emulsions are especially those that permit relatively long dwell times with sufficiently good mixing and good heat transfer with the simultaneous removal of the gaseous ammonia that forms during the hydrolysis.

Especially suitable are so-called "List reactors" (manufacturer: List AG, CH-4422 Arisdorf, Switzerland) having a free volume of up to 16.5 m$^3$, which are constructed as either single-shaft or twin-shaft devices and have special mixing and scraping members both on the shaft and in the reactor housing. Such reactors may also be connected in series, as a result of which a high degree of flexibility in use can be achieved.

According to DE-A 196 00 163, when the hydrolysis is complete the reaction mixture may be continuously introduced directly from the List reactor into a precipitation reactor equipped with a high-speed stirrer and containing a low-boiling alcohol, for example methanol or ethanol. The superabsorbent polymer precipitates thereby in the form of a fine, readily filterable powder. Drying and grinding to the desired particle size yield the finished superabsorber.

It is also described that, in order to neutralise the unconsumed alkali metal hydroxide or to adjust the pH value of the end product, acid is added in order to obtain the pH value required for use in hygiene articles, for example babies' nappies or incontinence articles for adults, which value is to be from 5.5 to 6.5.

Since alcohols must be used in the known process to isolate the product, the alcohol/water/salt mixture formed after the neutralization must be disposed of, or the alcohol is returned to the production process after it has been separated off. For reasons of explosion protection, drying of the SAP containing water and alcohol is possible only with a great financial outlay. For economic and ecological reasons, use is often made of other processes.

According to DE-A 196 00 163, it is said to be possible, as an alternative to working up with alcohols, to dry the hydrolysis product in vacuo at temperatures up to 100° C. Without neutralization of the unconsumed alkali metal hydroxide, the products have a pH value, greater than 7.0, which is too high for use in hygiene articles, for example babies' nappies or incontinence articles for adults.

DETAILED DESCRIPTION OF THE INVENTION

Accordingly, the object of the present invention is to provide an SAP having a pH value of less than or equal to 7 by a process entailing alkaline hydrolysis of PAN emulsions or PAN precipitation polymers, without the need to use alcohols or any other organic solvents for isolation.

The invention provides a process for the preparation of SAP's, which comprises the following subsidiary steps:

a) preparing a PAN emulsion (as described above according to DE-A 42 33 026 and its corresponding U.S. Pat. No. 5,356,985 that is incorporated by reference herein), preferably uncrosslinked or crosslinked homopolymers of acrylonitrile, b) subjecting the emulsion obtained in a) to alkaline hydrolysis in self-cleaning reactors suitable for high-viscosity media to obtain a hydrolysate, c) neutralizing the hydrolysate by:
  1. adding acid to the hydrolysate, or
  2. adding the hydrolysate to a water/acid mixture in order to adjust the pH value, to obtain a water-containing, gel-like product, and d) drying of the water-containing, gel-like product, e) granulating the dry product obtained in d) to the desired particle size, f) modifying the surface modification of the granular SAP obtained in e).

Reactors suitable for high viscosity medium are these that are known in the art for handling gel-like compounds.

It has been found that, in contrast to DE-A 196 00 163, an organic solvent is not necessary for isolation of the SAP in the process according to the invention. It is also important that acid is added (according to c1.)) to the hydrolysate in order to neutralise the alkali metal hydroxide and adjust the pH value. In contrast to DE-A 196 00 163, the salts that form thereby remain in the product after drying. It is surprising that outstanding properties are obtained even in the presence of the salt originating from the neutralization. Alternatively, it is also possible for the purposes of neutralization to add the resulting hydrolysate to a mixture consisting of water/acid (according to c2.)) and isolate it again some time later. The low molecular weight salts that form thereby are washed out or remain in the liquor. The properties of the products obtained by that process are likewise outstanding.

The PAN emulsions according to subsidiary step a) have a mean particle size, determined by laser correlation spectroscopy, of from 60 to 500 nm, preferably from 80 to 200 nm, and a solids content of from 10 to 55 wt. %. The molecular weights (weight-average) of the uncrosslinked PAN emulsions are from $5*10^5$ to $1*10^7$ g/mol. Preferred PAN emulsions are uncrosslinked or crosslinked homopolymers of acrylonitrile. Crosslinked PAN emulsions contain polyfunctional monomers incorporated by polymerization, as described in DE-A 42 33 026, of from 0.2 to 4.0 wt. %, based on the total amount of monomers.

According to subsidiary step b), the low-viscosity starting materials (PAN emulsion and aqueous alkali metal hydroxide solution) are mixed, and the hydrolysis is carried out in self-cleaning reactors suitable for high-viscosity media (HV reactors). In the hydrolysis, high-viscosity gels having a solids content of from 10 to 70 wt. % are formed. Suitable HV reactors have a good mixing and kneading action for the high-viscosity gel that forms, good heat transfer, and permit removal of the ammonia that forms in the hydrolysis. Especially suitable HV reactors are those from List AG, CH-4422 Arisdorf, Switzerland, which are constructed as single- or twin-shaft devices and have mixing and scraping members both on the shaft and in the reactor housing.

After the starting materials have been mixed, the hydrolysis may be carried out in a batch process, in a semi-continuous process by the metering in of one or both starting materials, or in a continuous process. In the case of a continuous process it is also possible to meter in the starting materials at the beginning of the process or in part later in the process. It is possible to use one or more HV reactors connected in series. Mixing of the starting materials may be carried out in the HV reactor or apparatuses located upstream thereof, such as, for example, pipes or static mixers, or alternatively in an HV reactor located upstream, the principal function of which is mixing, or in screw-type kneading machines.

In the hydrolysis of the PAN emulsions with aqueous alkali metal hydroxide solutions, the molar ratio of the nitrile groups of the polymer to the alkali metal hydroxide is from 1:1 to 1:0.05, preferably from 1:0.9 to 1:0.1, especially from 1:0.7 to 1:0.3. Alkali metal hydroxides are preferably NaOH or KOH or mixtures thereof. The hydrolysis may be carried out at from 80 to 200° C., preferably from above 100 to 160° C., under pressure. The reaction times are from 0.01 to 10 hours. The gaseous ammonia that forms in the hydrolysis may be removed from the reactor and dissolved in water or condensed at low temperatures. In order to remove the ammonia from the hydrolysis product as completely as possible, it is advantageous to evaporate off water from the reactor in addition to ammonia. The resulting loss of water can be compensated by the metered addition of water (in liquid or in vapor form). However, it is also possible not to compensate the resulting loss, so that the solids content of the hydrolysis product increases accordingly.

In the hydrolysis there form partially hydrolyzed polymers in which from 30 to 80 mol % of the nitrile groups of the PAN polymer have been converted into carboxylate groups and from 20 to 70 mol % into carboxamide groups and from 0 to 20 mol % of the nitrile groups remain unchanged. The pH value of the hydrolysis products, measured as a 0.1 wt. % solution in 0.9 wt. % NaCl solution, is in the region of 8.0, preferably from 7.5 to 7.1.

According to subsidiary step c), in order to adjust the pH to a value in the region of 7.0, preferably from 6.5 to 5.5, measured as a 0.1 wt. % solution in 0.9 wt. % NaCl solution, an acid is added to the hydrolysis product (according to c1.)) when the hydrolysis is complete, or the hydrolysis product is passed for a short dwell time into a water/acid mixture (according to c2.)).

Suitable acids according to c1.) include mineral acids, such as, for example, hydrochloric acid, sulfuric acid, phosphoric acid, nitric acid, carboxylic acids, also polyvalent acids and acids having further functional groups, for example formic acid, acetic acid, propionic acid, adipic acid, lactic acid, citric acid, polymeric acids, for example polyacrylic acid, polyacrylic acid copolymers, polystyrenesulfonic acid, and mixtures of the above-mentioned acids. Polymeric acids may be used in crosslinked or uncrosslinked form.

The amount of acid added in subsidiary step c1.) is dependent on the one hand on the pH value desired for the particular application and on the other hand on the acid strength of the acid. Accordingly, the amount of acid added is from 0.1 to 20 wt. %, preferably from 0.1 to 10 wt. %, based on the dry weight of the hydrolysis product. The alkali metal salts formed by the addition of the acid remain in the product. The acid may be mixed with the high-viscosity hydrolysis product continuously or discontinuously in suitable mixers, such as, for example, static mixers, screw-type kneading machines, and kneaders.

Suitable acids according to c2.) include mineral acids, such as, for example, hydrochloric acid, sulfuric acid, phosphoric acid, nitric acid, carboxylic acids, also polyvalent acids and acids having further functional groups, for example formic acid, acetic acid, propionic acid, adipic acid, lactic acid, citric acid, polymeric acids, for example polyacrylic acid, polyacrylic acid copolymers, polystyrenesulfonic acid, and mixtures of the above-mentioned acids. Polymeric acids may be used in crosslinked or uncrosslinked form.

The amount of acid added in subsidiary step c2.) is dependent on the one hand on the pH value desired for the particular application and on the other hand on the acid strength of the acid. Accordingly, the amount of acid added is from 0.1 to 20 wt. %, preferably from 0.1 to 10 wt. %, based on the dry weight of the hydrolysis product. The acid is dissolved in from 1.0 to 100 times the amount of water, preferably from 1.5 to 30 times the amount of water, based on the weight of the SAP gel to be neutralized. The dwell time of the hydrolysate in the water/acid mixture is from 5 seconds to 30 minutes, preferably from 10 seconds to 5 minutes. Neutralization of the hydrolysis product according to subsidiary step c2.) may be carried out both batchwise and continuously.

The water-containing, gel-like product obtained according to subsidiary step c) is dried according to subsidiary step d). Suitable methods of drying are described in "Modem Superabsorbent Polymer Technology", Eds. F. L. Buchholz, A. T. Graham, Wiley-VCH, New York, 1998, ISBN 0-471-19411-5, Chapter 3.2.4.2. Post-Reactor Gel Preparation, p. 85–87 and 3.2.5. Drying, p. 87–93 and the literature cited therein. In contrast to DE 196 00 163 A1, the salts formed by the addition of an acid according to subsidiary step c1.) remain in the product after drying.

In subsidiary step e), the dried product is ground and sized according to the prior art; see in this connection: "Modem Superabsorbent Polymer Technology", Eds. F. L. Buchholz, A. T. Graham, Wiley-VCH, New York, 1998, ISBN 0-471-19411-5, Chapter 3.2.6. Handling of the Dried Material: Particle Sizing, p. 93–95. The particle-size distribution of the ground and sized SAP is to be in the range of from 100 to 1000 μm, preferably from 150 to 850 μm.

Surface modification, such as crosslinking, of the granular SAP's is indicated in the instances where the material is to be used in hygiene articles, such as babies' diapers. Gel blocking which leads to low transport rate of the absorbed liquid may be avoided and better absorptive properties are attained by such modification.

It is important that further acid may be added in subsidiary step f) in order to adjust the pH value. It is possible to use the same acid as in subsidiary step c) or a different acid from the above-mentioned group of acids. This acid may be used in amounts of from 0 to 10 wt. %, preferably from 0 to 6 wt. %, based on SAP together with the agent for surface crosslinking.

Preferred surface-modifying agents where an acid is used are di- and poly-ols, for example ethylene glycol, 1,2-propanediol, glycerol, trimethylolpropane. Those modifying agents are sprayed onto the SAP particles together with the acid in solution, the solution usually consisting of an alcohol/water mixture, and mixed and made to react in the course of from 0.1 to 5 hours, preferably from 0.5 to 3 hours, at from 100 to 200° C., preferably from 110 to 180° C. However, it is also possible to use the above-mentioned surface-modifying agents without an acid. Also suitable are ethylene carbonate, diglycidyl compounds, such as, for example, ethylene glycol diglycidyl ether, or di- or poly-isocyanates, and optionally mixtures of the mentioned agents.

The SAP's obtainable by the process according to the invention are excellently suitable for use in the manufacture of hygiene articles, such as, for example, babies' nappies, incontinence articles for adults and feminine hygiene, for the covering of electric cables, for use as water-storage materials in agriculture, and for the packaging sector of goods that are at risk of leaking.

For the characterization of the products, the absorption (according to EDANA 440.0-96), retention (according to EDANA 441.0-96), AUL at 0.3 and 0.7 psi (according to EDANA 442.0-96) and the pH value (0.1 wt. % solution in 0.9 wt. % NaCl solution) are measured.

EXAMPLES 1–3

Hydrolysis

The alkaline hydrolyses of the PAN emulsions were carried out in a continuous process, consisting of a twin-shaft extruder (reaction volume: 0.5 liter) and an HV reactor from List (List DTB 6 Conti, reaction volume 17.5 liters).

The PAN emulsion was prepared according to DE- 42 33 026 A1 (U.S. Pat. No. 5,356,985), Example 8. The emulsion is an uncrosslinked polyacrylonitrile homopolymer, and the amount of polymeric emulsifier used, in contrast to DE 42 33 026 A1, Example 8, was only 2.5 wt. %, based on polyacrylonitrile.

The starting materials (PAN emulsion, sodium hydroxide solution, deionised water) were pumped into the twin-shaft extruder (metering flow rates, speed and heating temperature of the extruder: see Table 1). The viscous product that left the extruder was metered into the HV reactor. After passing through the HV reactor, the viscous, gel-like, slightly yellow to colorless product was discharged from the delivery screw via a multi-hole nozzle (heating temperature, speed of the main shaft of the HV reactor and of the delivery screw: see Table 1). The resulting ammonia/water mixture is relieved from the HV reactor via a pressure-maintaining device into an acid washing apparatus.

EXAMPLES 1a, 2a

Neutralization in Subsidiary Step c1.)

Table 2 shows the acids used in subsidiary step c1.) (Example 1a, 2a) for adjusting the pH value, and the amounts in wt. %, based on the solids content of the gel-like SAP. After addition of the acid and mixing in a kneader, the gel is dried in a laboratory drying cabinet at from 110 to 115° C., ground by means of a laboratory mill and fractionated to a particle size of from 100 to 800 μm.

Surface modification was carried out using a solution of ethylene glycol diglycidyl ether, 1,2-propanediol and water in a ratio of 0.06:3.152:0.788. To that end, 100 parts of SAP powder were placed in a glass beaker, sprayed and mixed with 4 parts of the above-mentioned solution, and then reacted for 2 hours at 125° C. in a drying cabinet (see Table 2).

EXAMPLES 1b–3b

Surface Modification in Subsidiary Step f)

Table 3 shows the acids used in subsidiary step c1.) and in subsidiary step f) for adjusting the pH value and/or as catalyst for the surface modification, and the amounts in wt. %, based on the solids content of the gel-like SAP. After addition and mixing of the acid in subsidiary step c), the gel is dried in a laboratory drying cabinet at from 110 to 115° C., ground by means of a laboratory mill and fractionated to a particle size of from 100 to 800 μm.

Table 3 additionally shows an example in which the neutralization was carried out according to subsidiary step c2.) (Example 3b). The moist SAP gel was suspended in five times the amount of water; 85% formic acid was added in the amount indicated in wt. % in Table 3, based on the solids content of the gel-like SAP, and the gel-like SAP was isolated after 60 seconds. The resulting gel was worked up further as described above.

The surface modification is carried out using a solution of acid, as indicated in Table 3, glycerol, 2-propanol and water in a ratio of 1:2:2:2. To that end, 100 parts of SAP powder are placed in a glass beaker, sprayed and mixed with 7 parts of the above-mentioned solution, and then reacted for 2 hours at 160° C. in a drying cabinet.

TABLE 1

Hydrolysis conditions in the twin-shaft extruder and the HV reactor

| Example | PAN emulsion [wt. %] | PAN emulsion [kg/h] | NaOH 45% [kg/h] | Heating temperature Extruder [° C.] | Speed Extruder [rpm] | Heating temperature HV reactor [° C.] | Speed HV reactor [rpm] | Speed Delivery screw [rpm] | pH value |
|---|---|---|---|---|---|---|---|---|---|
| 1 | 25 | 8.0 | 1.7 | 130 | 70 | 110 | 20 | 75 | 8.01 |
| 2 | 20 | 8.56 | 1.44 | 130 | 100 | 110 | 20 | 75 | 7.54 |

TABLE 2

Neutralization, subsidiary step c)

| Example | Gel Example | Acid in subsidiary step c) | Amount [wt. %] | pH value | Retention | AUL 0.3 psi |
|---|---|---|---|---|---|---|
| 1a | 1 | Lactic acid | 4 | 6.71 | 37 | 28.2 |
| 2a | 2 | Lactic acid | 4 | 6.56 | 27 | 24.6 |

TABLE 3

Surface modification, subsidiary step f)

| Example | Gel Example | Acid in subsidiary step c1.) | Acid in subsidiary step c2.) | Amount [wt. %] | Acid in step f) | Amount [wt. %] |
|---|---|---|---|---|---|---|
| 1b | 1 | Lactic acid | | 4 | Lactic acid | 1 |
| 2b | 2 | Lactic acid | | 4 | Lactic acid | 1 |
| 3b | 2 | | Formic acid (85%) | 5.4 | Lactic acid | 1 |

| Example | pH value | Absorption | Retention | AUL 0.3 psi | AUL 0.7 psi |
|---|---|---|---|---|---|
| 1b | 6.69 | | 29.4 | 23.7 | |
| 2b | 6.56 | | 30 | 28.6 | |
| 3b | 6.25 | 46.5 | | 29.9 | 21.5 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a superabsorbent polymer (SAP) comprising:
   (a) subjecting a polyacrylonitrile (PAN) emulsion to alkaline hydrolysis to obtain a hydrolysate;
   (b) adding the hydrolysate to a water/acid mixture to produce a water-containing, gel-like superabsorbent polymer (SAP);
   (c) isolating the superabsorbent polymer (SAP), neither alcohols nor organic solvents being used in the isolating step;
   (d) drying the superabsorbent polymer (SAP) of step (c);
   (e) grinding the dry superabsorbent polymer (SAP); and
   (f) crosslinking the surface of the ground superabsorbent polymer (SAP) by means of,
      (i) spraying at least one surface modifying agent together with an acid solution onto the surface of the ground superabsorbent polymer (SAP),
      (ii) mixing the surface sprayed superabsorbent polymer (SAP), and
      (iii) heating the surface sprayed superabsorbent polymer (SAP) of step (ii) to a temperature of 100° to 200°.

2. The process of claim 1, wherein the hydrolysis is carried out in a self-cleaning reactor suitable for high-viscosity media, and wherein the resulting hydrolysate is neutralized.

3. The process of claim 2, wherein the neutralization is carried out by at least one of adding acid to said hydrolysate and adding said hydrolysate to a water/acid mixture.

4. The process of claim 1, wherein the polyacrylonitrile (PAN) emulsion comprises a homopolymer of acrylonitrile.

5. The process of claim 1, the emulsion has a mean particle size of 60 to 500 nm.

6. The process of claim 1, wherein the polyacrylonitrile (PAN) has a weight average molecular weight of $5 \times 10^5$ to $1 \times 10^7$ g/mol.

7. The process of claim 1, wherein the hydrolysate comprises gels having a solids content of from 10 to 70 wt. %.

8. The process of claim 1, wherein the particle-size of the ground superabsorbent polymer (SAP) is from 100 to 1000 μm.

9. The superabsorbent polymer (SAP) prepared according to the process of claim 1.

10. An article selected from the group consisting of diapers (nappies), incontinence articles, water-storage materials and electric cable coverings comprising the superabsorbent polymer (SAP) of claim 9.

11. The process of claim 4, wherein the homopolymer of acrylonitrile is uncrosslinked.

12. The process of claim 4, wherein the homopolymer of acrylonitrile is crosslinked.

13. A process for preparing a superabsorbent polymer (SAP) comprising:
   (a) subjecting a polyacrylonitrile (PAN) emulsion to alkaline hydrolysis in a self-cleaning reactor suitable for high-viscosity media to produce a hydrolysate;
   (b) neutralizing the hydrolysate with an acid and/or in an acid/water mixture to produce a water-containing, gel-like superabsorbent polymer (SAP);
   (c) drying the superabsorbent polymer (SAP);
   (d) granulating the superabsorbent polymer (SAP) to a desired particle size; and
   (e) modifying the surface of the granulated superabsorbent polymer (SAP) by means of,
      (i) spraying at least one surface modifying agent together with an acid solution onto the surface of the granulated superabsorbent polymer (SAP),
      (ii) mixing the surface sprayed superabsorbent polymer (SAP), and
      (iii) heating the surface sprayed superabsorbent polymer (SAP) of step (ii) to a temperature of 100° C. to 200° C.

14. The process of claim 13, wherein the hydrolysate is adjusted to between pH 5.5 to 6.5 in the neutralizing step.

15. The process of claim 13, wherein the acid is selected from the group consisting of hydrochloric acid, sulfuric acid, phosphoric acid, nitric acid, formic acid, acetic acid, propionic acid, adipic acid, lactic acid, citric acid, polyacrylic acid, polyacrylic acid copolymers, polystyrenesulfonic acid, and mixtures thereof.

16. The process of claim 13 wherein the modifying agent of step (e)(i) is selected from diols, polyols and mixtures thereof.

17. The process of claim 16 herein the modifying agent of step (e)(i) is selected from ethylene glycol, 1,2-propanediol, glycerol, trimethyloipropane and mixtures thereof.

18. The process of claim 1 wherein the modifying agent of step (f)(i) is selected from diols, polyols and mixtures thereof.

19. The process of claim 18 wherein the modifying agent of step (f)(i) is selected from ethylene glycol, 1,2-propanediol, glycerol, trimethylolpropane and mixtures thereof.

* * * * *